(12) United States Patent
Sanders et al.

(10) Patent No.: US 10,213,297 B2
(45) Date of Patent: Feb. 26, 2019

(54) CONTROLLING TISSUE ENGINEERED HEART VALVE GEOMETRY BY USING PREDEFINED INSERTS DURING CULTURE

(71) Applicants: Technische Universiteit Eindhoven, AZ Eindhoven (NL); Universitaet Zuerich, Zurich (CH)

(72) Inventors: Bart Sanders, SP Eindhoven (NL); Sandra Vossen-Loerakker, GL Eindhoven (NL); Anita Driessen-Mol, JM Rosmalen (NL); Simon Philipp Hoerstrup, Zurich (CH); Franciscus Petrus Thomas Baaijens, DB Eindhoven (NL)

(73) Assignees: UNIVERSITAET ZUERICH, Zurich (CH); TECHNISCHE UNIVERSITEIT EINDHOVEN, Eindhoven (NL)

( * ) Notice: Subject to any disclaimer, the term of this patent is extended or adjusted under 35 U.S.C. 154(b) by 211 days.

(21) Appl. No.: 15/024,857

(22) PCT Filed: Sep. 24, 2014

(86) PCT No.: PCT/EP2014/070352
§ 371 (c)(1),
(2) Date: Mar. 25, 2016

(87) PCT Pub. No.: WO2015/044190
PCT Pub. Date: Apr. 2, 2015

(65) Prior Publication Data
US 2016/0235527 A1    Aug. 18, 2016

Related U.S. Application Data

(60) Provisional application No. 61/883,870, filed on Sep. 27, 2013.

(51) Int. Cl.
*A61F 2/00* (2006.01)
*A61F 2/24* (2006.01)
(Continued)

(52) U.S. Cl.
CPC .......... *A61F 2/2415* (2013.01); *C12M 21/08* (2013.01); *C12M 25/00* (2013.01); *C12M 29/04* (2013.01); *A61F 2/0077* (2013.01); *A61F 2/2472* (2013.01)

(58) Field of Classification Search
CPC .... A61F 2/2415; A61F 2/0077; A61F 2/2472; C12M 21/08; C12M 25/00; C12M 29/04
See application file for complete search history.

(56) References Cited

U.S. PATENT DOCUMENTS

2008/0131965 A1    6/2008   Baaijens
2012/0244617 A1    9/2012   Seyedhamed et al.

FOREIGN PATENT DOCUMENTS

EP    1864687 A1    12/2007
GB    1243375 A     8/1971
(Continued)

OTHER PUBLICATIONS

"Announcement", Chemistry & Industry, Society of Chemical Industry, London, GB, No. 9, May 1, 1995, p. 330, XP000505203, ISSN: 0009-3068 the whole document.
(Continued)

*Primary Examiner* — Gautam Prakash
(74) *Attorney, Agent, or Firm* — Agris & Von Natzmer, LLP; Joyce Von Natzmer

(57) ABSTRACT

Various inserts, called shapers and spacers, are provided for controlling tissue engineered heart valve (TEHV) leaflet geometry during culture. These inserts will prevent TEHV leaflet retraction during culture, be able to control the leaflet geometry during culture, enable culturing TEHV leaflets
(Continued)

with a larger coaptation area, control the height of the coaptation area, maintain TEHV leaflet curvatures, and/or enable possibilities to culture TEHV leaflets in open configuration.

9 Claims, 26 Drawing Sheets

(51) Int. Cl.
    *C12M 1/00*     (2006.01)
    *C12M 1/12*     (2006.01)
    *C12M 3/00*     (2006.01)

(56) References Cited

FOREIGN PATENT DOCUMENTS

| JP | 4738720 A | 9/1972 |
| JP | 2009539439 A | 11/2009 |

OTHER PUBLICATIONS

Loerakker et al., Effects of valve geometry and tissue anisotropy on the radial stretch and coaptation area of tissue-engineered heart valves, Journal of Biomechanics 46, 2013,1792-1800.
Japanese Office Action of corresponding Japanese application 2016518169 dated Jun. 5, 2018, English translation of Japanese Office Action dated Jun. 5, 2018.

CONTROLLING TISSUE ENGINEERED HEART VALVE GEOMETRY BY USING PREDEFINED INSERTS DURING CULTURE

FIELD OF THE INVENTION

This invention relates to devices for tissue engineering. In particular, the invention relates to devices for tissue engineering heart valves.

BACKGROUND OF THE INVENTION

Tissue engineered heart valves (TEHV) are produced by seeding cells on a heart valve shaped scaffold material, followed by a culturing period in a bioreactor system. During culture, the cells will produce an extracellular matrix (ECM).

So far no solutions are available to control heart valve geometry during culture. Contractile cells that are being used will compact the new-formed tissue in all possible directions of constrain. Any predefined scaffold geometry at the start of culture will therefore be lost during culture, resulting in an entirely different geometry after culture compared to the imposed starter geometry.

There are two ways of culturing the TEHV. The first method is to culture the TEHVs in a so-called "open configuration". This means that the individual heart valve leaflets are separated from each other during culture. The benefit of this approach is that the TEHV leaflets do not have to be separated after culture. The problem with this approach is that because cells will build up tension during culture, they will retract the leaflets, which results in shorted leaflets. In addition, because of the internal tension that builds up in the leaflets, the initially curved shape of the scaffold may be straightened thereby compromising the desired curvature of the leaflets and functionality of the valve.

The second method is to culture the TEHV in a "closed configuration". This means that the valve leaflets are attached to each other, which prevents shortening of the leaflets due to the internal tension that builds up in the leaflets during culture. However, it does not prevent 'straightening' or 'flattening' of the leaflets. In addition, it has been proven to be difficult to achieve a sufficiently large coaptation area between the leaflets in this way, which is crucial for in vivo functionality of the heart valve.

The present invention addresses these problems and provides devices, which allow for the maintenance and control of heart valve geometry during culture.

SUMMARY OF THE INVENTION

The present invention provides devices, methods of using these devices and systems for controlling tissue engineered heart valve leaflet geometry by using predefined inserts during tissue culture. The inserts are referred to herein as (leaflet) shapers and (leaflet) spacers, which can be used individually or in combination with each other mostly depending on the type of cells cultured with the tissue growth materials and level of geometry shaping/control.

The first insert is a leaflet shaper and has been described herein with several different variations of embodiments. Since we observed that the cells build up tension in all constrained directions, we make use of this effect by inserting a rigid, concave construct that has the shape of the leaflet. The tension that develops in the leaflets will cause the leaflets to compact against the shaper, which acts as a constraint and is capable of controlling the curvature and coaptation of the leaflets.

In some embodiments, the leaflet shaper is covered with small holes to achieve proper nutrient exchange between the medium and the tissue that compacts around the insert. The shaper does not cover the wall of the heart valve such that nutrients and oxygen can be supplied to the wall. Because the tissue compacts against the concave aspect of the shaper, there is no need for a second valve shaped insert/shaper on the other side of the valve leaflets.

The second insert is a leaflet spacer and has been described herein as one embodiment that can be used in combination with the various shapers. When the leaflets are cultured in a closed configuration, the spacer will prevent retraction of the leaflets in the radial direction to constrain the height, and therefore control the size of the coaptation area. It will also enable maintenance of a predefined coaptation area. Hence, this leaflet spacer will constrain the height of the leaflets. A second advantage of the leaflet spacer is to prevent the leaflets from merging over the coaptation area during culture. Since the spacer will be positioned in between the individual leaflets, there is no chance for leaflet concrescence.

An advantage of using the embodiments presented in this invention is that it can result in circumferential collagen orientation in the cultured heart valves, which is beneficial for heart valve functionality.

Another advantage of using the embodiments presented in this invention is that it enables us to culture heart valves without the need of using a complex bioreactor system. In fact, the use of a simple jar would be sufficient. One of the functions of the bioreactor system was to impose the right geometry to the valves by dynamically loading them. But this inserts can achieve the same objective, which is to constrain the imposed geometry.

BRIEF DESCRIPTION OF THE D WINGS

DETAILED DESCRIPTION

FIGS. 1-5 show a first embodiment of a shaper 100 for maintaining and controlling heart valve geometry during culture. Shaper 100 is intended for a heart valve with three leaflets and distinguishes a support base 110 and three inner arms 112 each capable of supporting a tissue growth material (not shown) to form one of the leaflets of the heart valve. In this embodiment, it is the mid-axis of the heart valve leaflets that will be constrained and controlled during culture.

Each of the inner arms 112 has a first portion 112' and a second portion 112", which is only indicated for one of the inner arms for clarity purposes. First portion 112' is disposed normal to support base 110 and disposed proximal to a center of support base 110. Second portion 112" is nonlinear and disposed distal to support base 110 and bends away from the center of support base 110.

Figure 1:
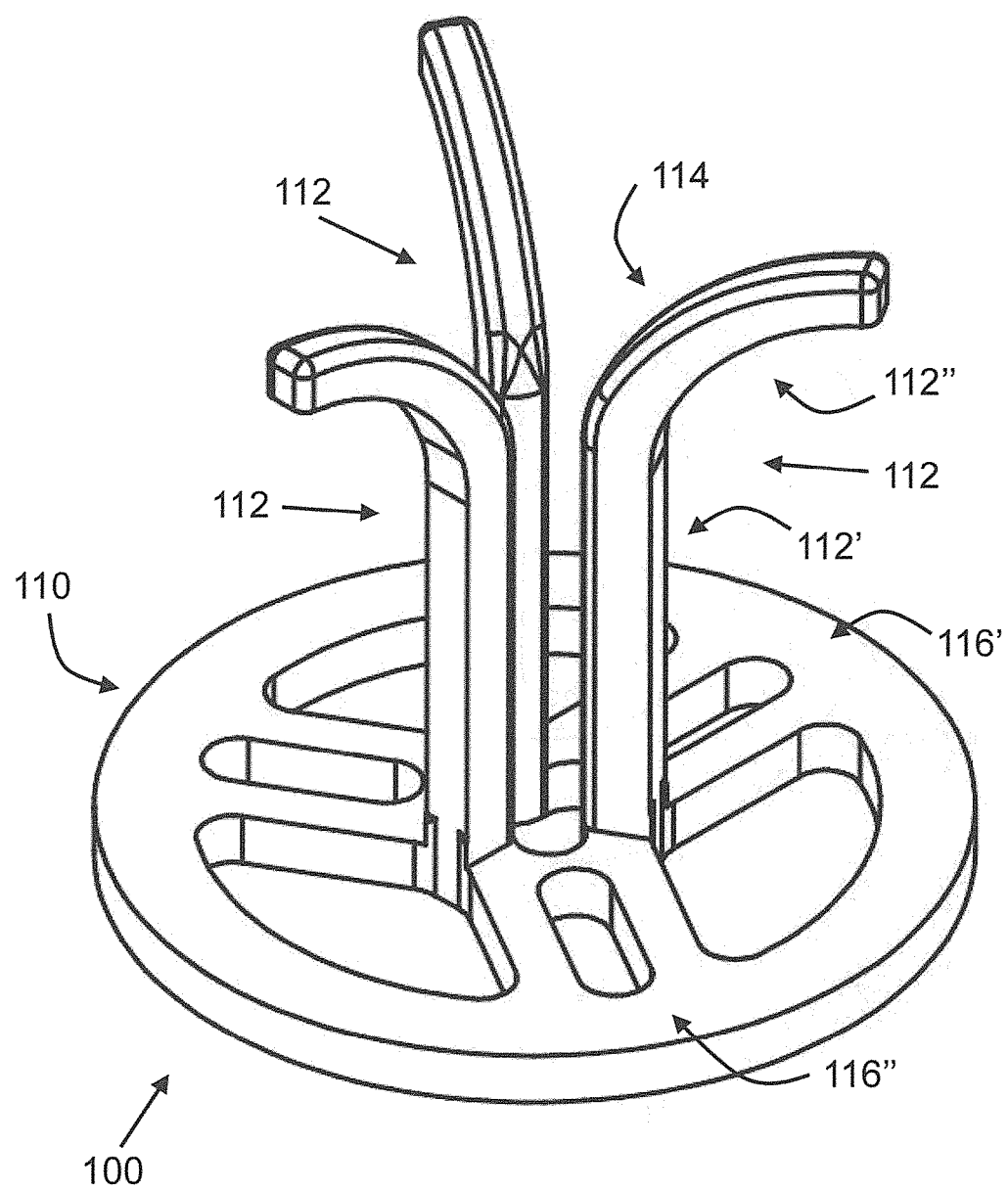
FIG. 1 shows according to an exemplary embodiment of the invention a three dimensional view of a shaper 100 for maintaining and controlling the shape of tissue growth material for three leaflets of a heart valve during tissue culture.
Figure 2:
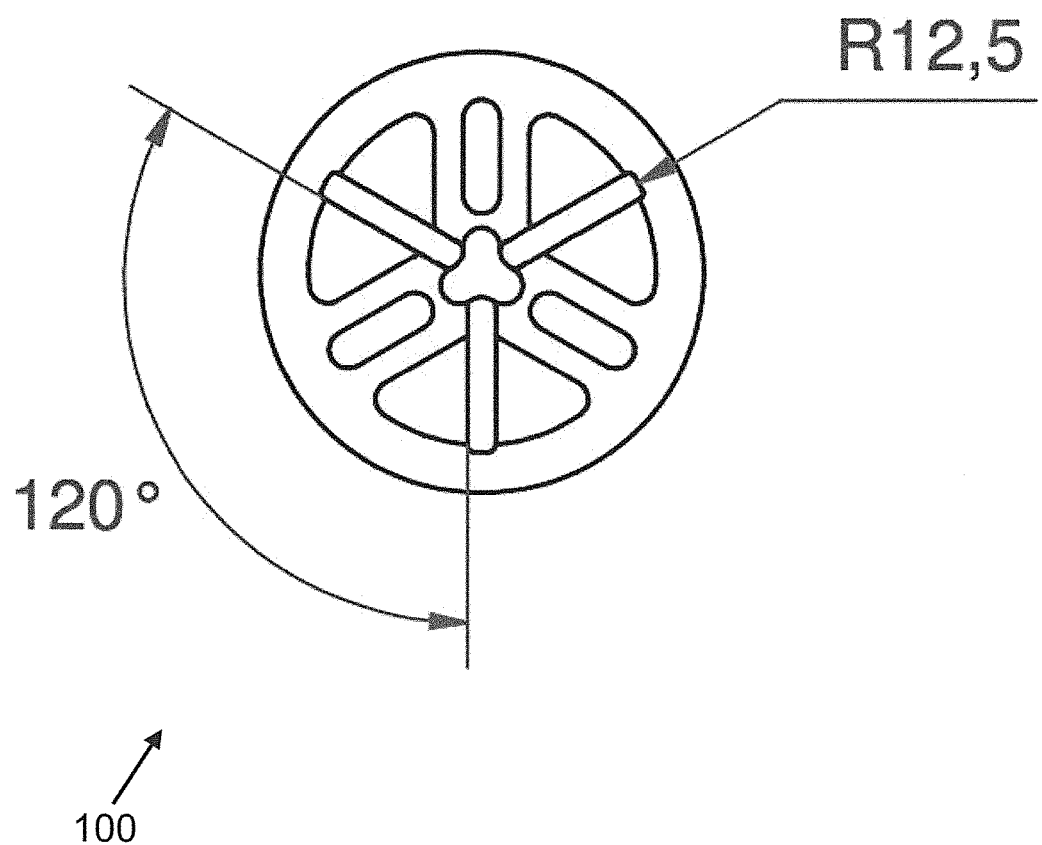
FIG. 2 shows according to an exemplary embodiment of the invention a top view of the shaper as shown in FIG. 1. The dimensions are in mm.
Figure 3:
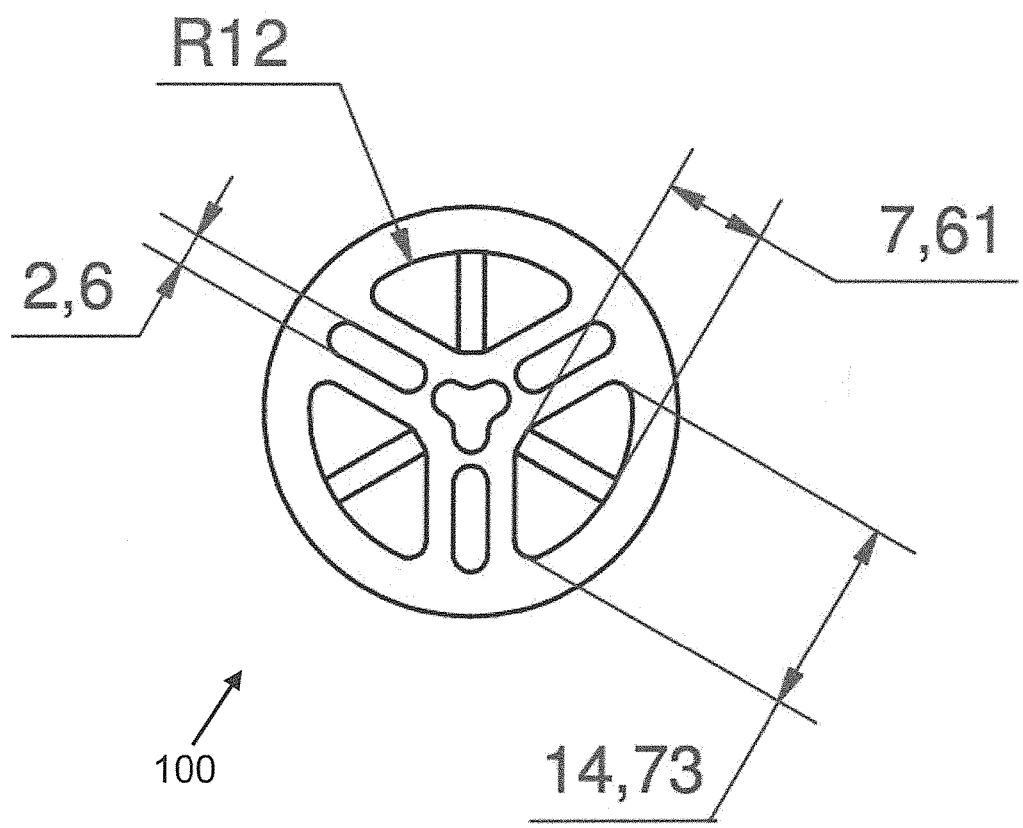
FIG. 3 shows according to an exemplary embodiment of the invention a bottom view of the shaper as shown in FIG. 1. The dimensions are in mm.
Figure 4:
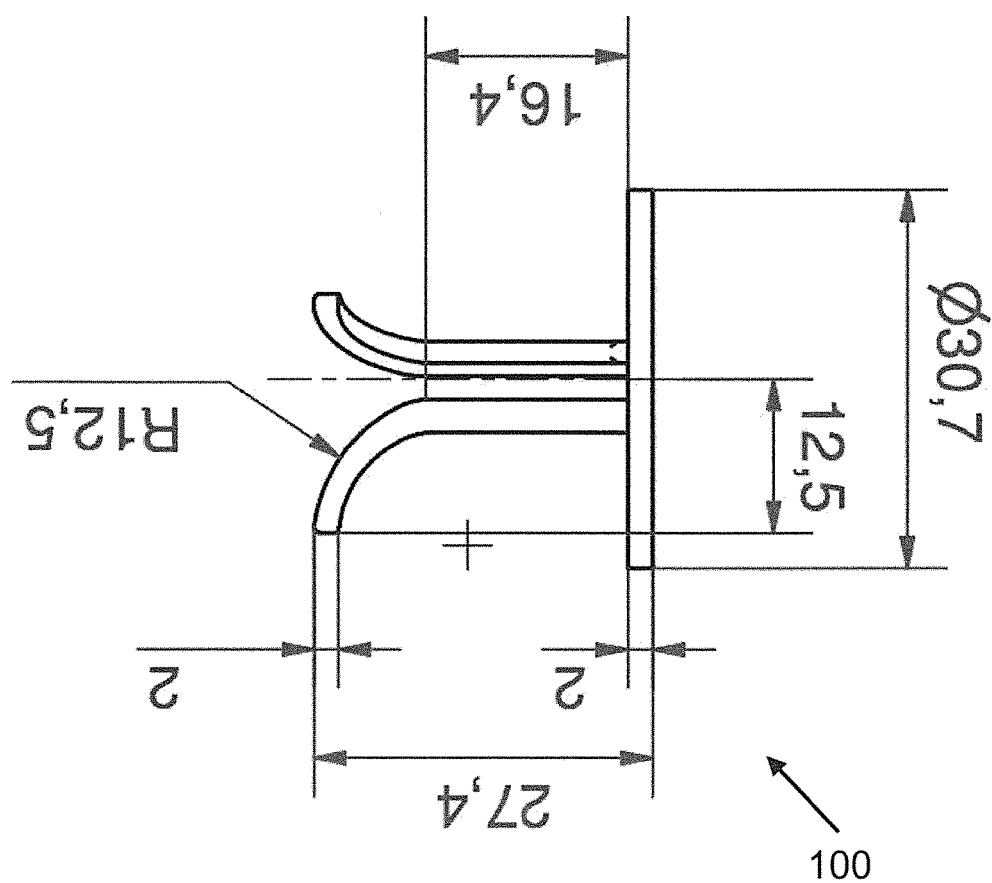
FIGS. 4-5 show according to an exemplary embodiment of the invention side views of the shaper as shown in FIG. 1. The dimensions are in mm.
Figure 5:
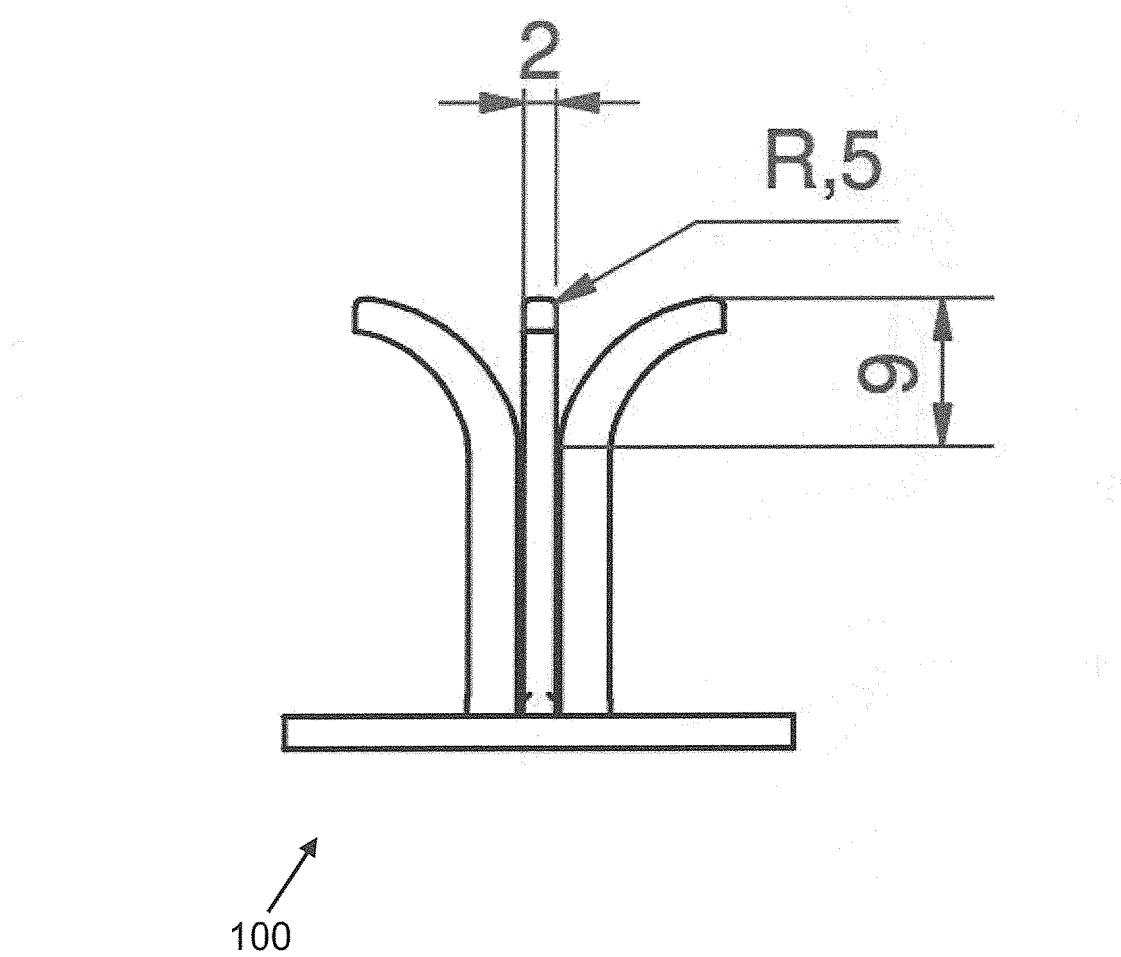

The inner arms 112 are distributed in a triangular pattern at support base 110 and are spaced from each other, as is evident in FIG. 1, to define enough space to fit at least the respective tissue growth materials. In other words, the tissue growth materials are placed over and against their respective inner arms 112 at the medial aspects 114 of inner arms 112 (114 is only indicated for one of the inner arms 112 for clarity purposes). In this embodiment, the respective tissue growth material is extended (not shown) to area 116' and 116" forming a wedge-shape growth material and a canopy (e.g. concave) draped over second portion 112".

FIGS. 2-5 show an exemplary embodiment of some dimensions of shaper 100, which are not limited to the invention as a person skilled in the art would readily appreciate that heart valves/leaflets would vary in dimensions and shape. A paper by the same group as the current inventors provides guidelines for some of the dimensions. The paper is entitled "Effects of valve geometry and tissue anisotropy on the radial stretch and coaptation area of tissue-engineered heart valves" by Loerakker et al. and published in Journal of Biomechanics 46 (2013) 1792-1800.

Depending on the type of cells used with the tissue growth material for shaper 100, there might be a desire to further control the shape and/or spacing between the tissue growth materials draped against the inner arms 112. For this purpose, spacer 1700 is designed with three surfaces 1710 distributed/oriented with respect to each other in the same triangular pattern as how inner arms 112 are distributed. Side 1720 of spacer 1700 can be placed towards the top of support base 110 and will then sit at the top of the support base 100 (see also FIG. 22). Surfaces 1710 fit in the space left to fit at least the tissue growth material to separate the tissue growth materials supported by each of the linear portions 112' of the inner arms 112. In other words, surfaces 1710 will separate the tissue growth materials.

Figure 6:
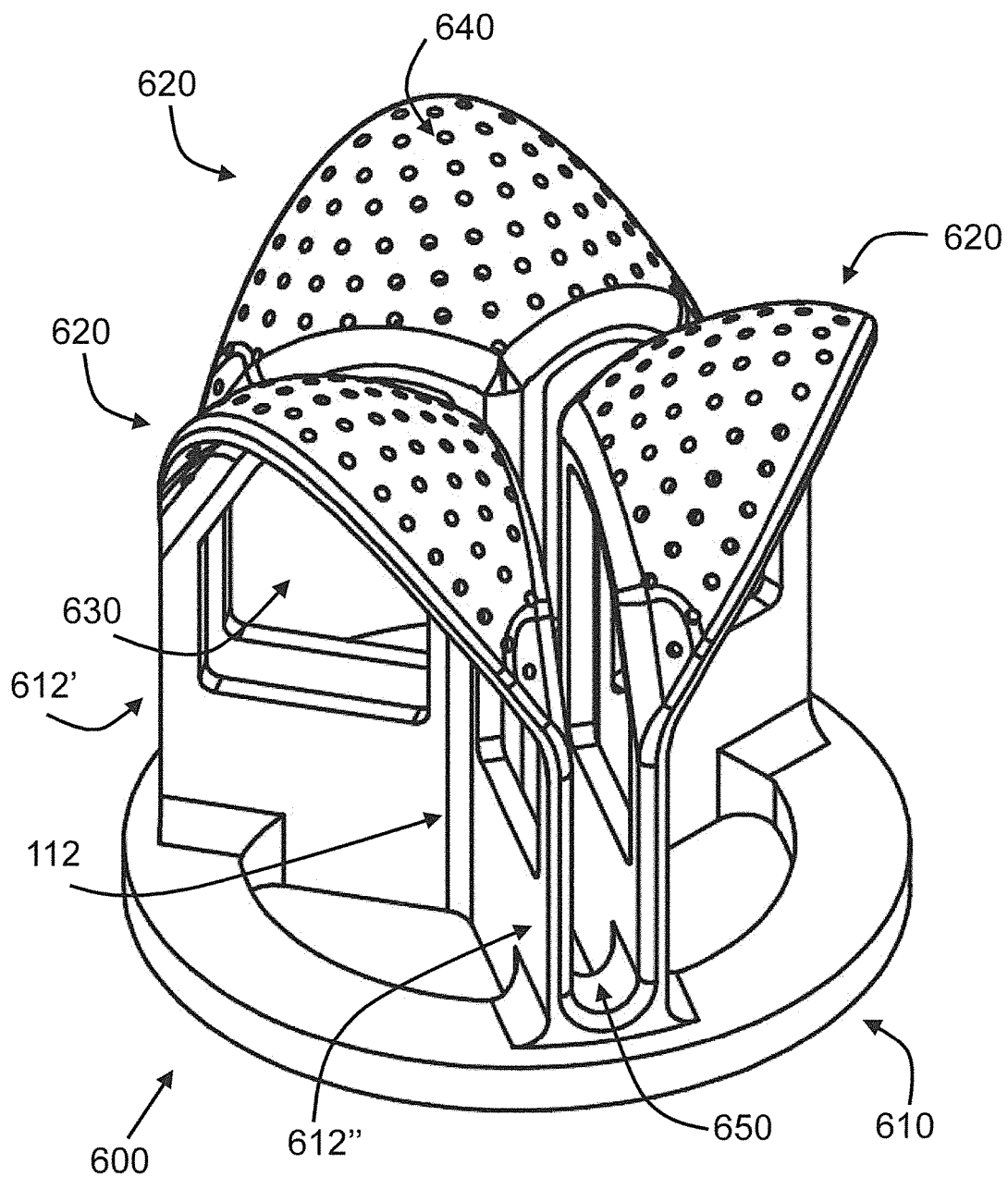
FIG. 6 shows according to an exemplary embodiment of the invention a three dimensional view of a shaper 600 for maintaining and controlling the shape of tissue growth material for three leaflets of a heart valve during tissue culture.

FIGS. 6-11 show a second embodiment of a shaper 600 for maintaining and controlling heart valve geometry during culture, where shaper 600 could be viewed as an extension of shaper 100 with similar structural components. Shaper 600 is intended for a heart valve with three leaflets and distinguishes a support base 610 and three canopy growth surfaces 620 expanded from the second portions of their respective inner arms 112. It is noted that only one inner arm 112 is indicated in FIG. 6 for clarity purposes.

Each canopy growth surface 620 is capable of supporting a tissue growth material (not shown) to form one of the leaflets of the heart valve. The canopy growth surfaces 620 define a concave surface when moving away from the center of support base 610 in outer direction.

The canopy growth surfaces 620 are supported by the respective first portions of the inner arms 112 and a pair of outer arms 612', 612" defined for each of the inner arms. Each of the outer arms 612', 612" have a first portion disposed normal to support base 610 and disposed distal to the center of support base 610.

In other words, each of the canopy growth surfaces 620 further span to the base of support surface 610 along the radial separation of the respective outer arms 612', 612" and inner arm 112 such that each span is capable of supporting the respective growth material. Differently stated, the combinations of each of the first portions of the inner arms 112 with their respective pair of outer arms 612', 612" define wedge-shape growth surfaces each capable of supporting the respective growth material. As a result the tissue growth material for the heart valve leaflets will be constraint and controlled during culture. Open area 630 (indicated for only one of the leaflet canopy growth surfaces for clarity purposes) is left open as it could enhance tissue formation. Holes 640 are intended to allow for improved exchange of nutrients.

The three canopy growth surfaces 620 are distributed in a triangular pattern at support base 610 and are spaced 650 from each other forming a star design, as is evident from e.g.

Figure 7:
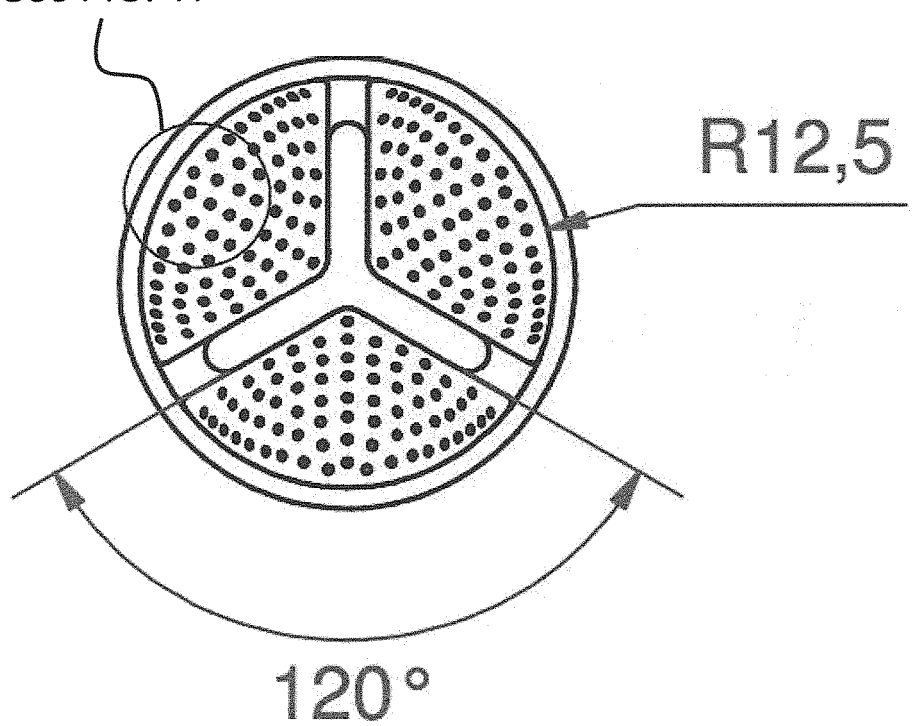
FIG. 7 shows according to an exemplary embodiment of the invention a top view of the shaper as shown in FIG. 6. The dimensions are in mm.
Figure 8:
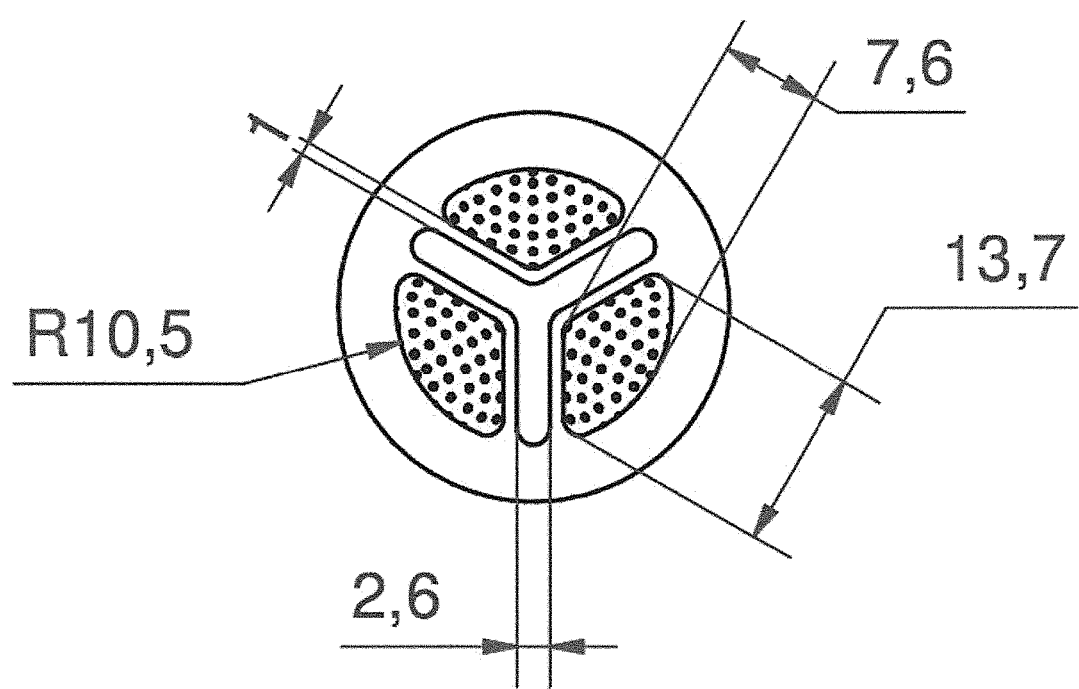
FIG. 8 shows according to an exemplary embodiment of the invention a bottom view of the shaper as shown in FIG. 6. The dimensions are in mm.
Figure 9:
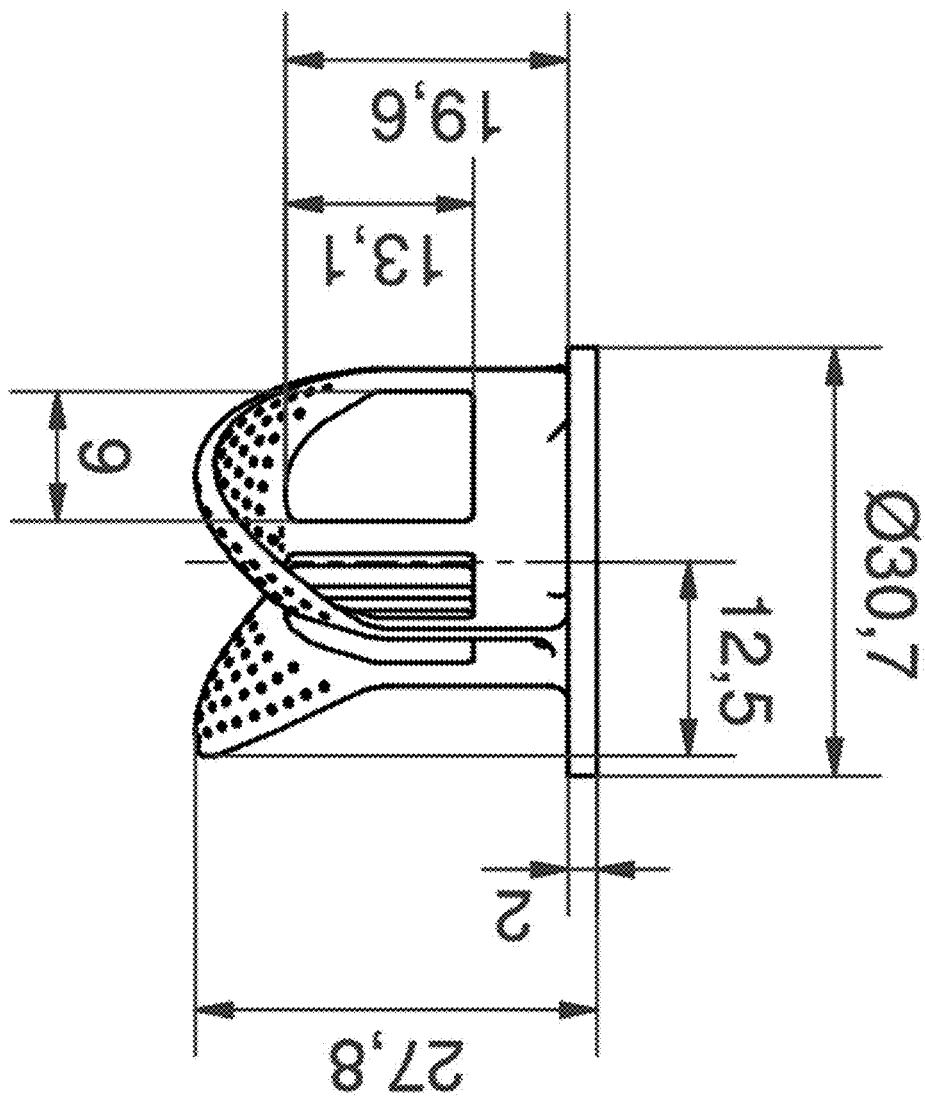
FIGS. 9-10 show according to an exemplary embodiment of the invention side views of the shaper as shown in FIG. 6. The dimensions are in mm.
Figure 10:
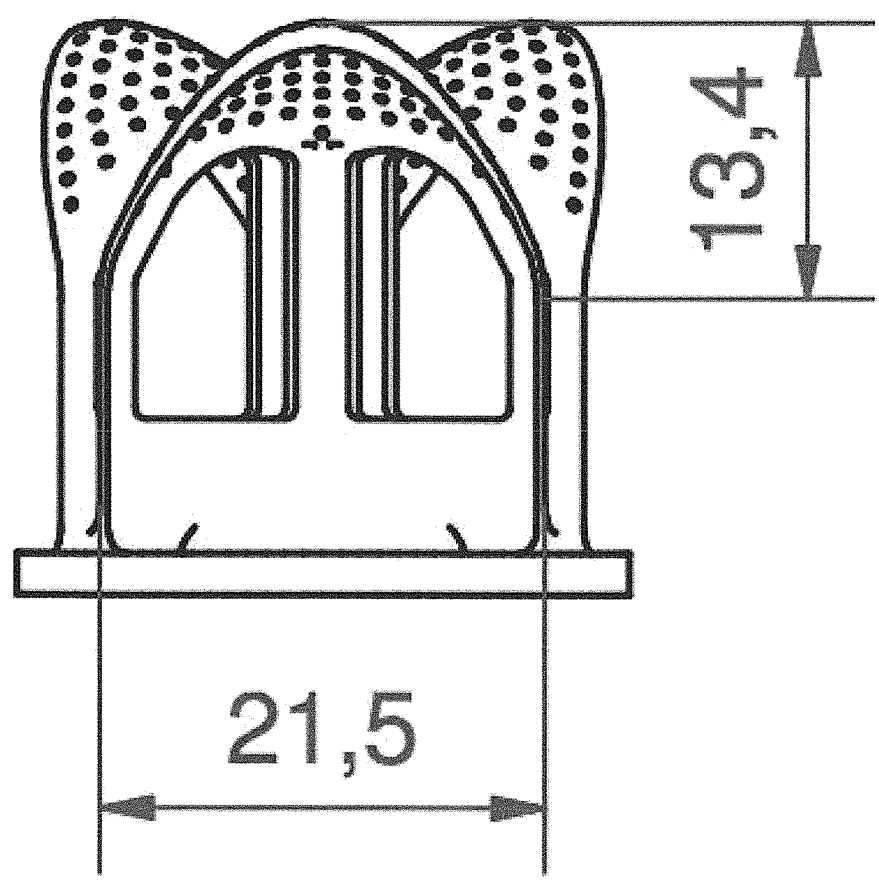
Figure 11:
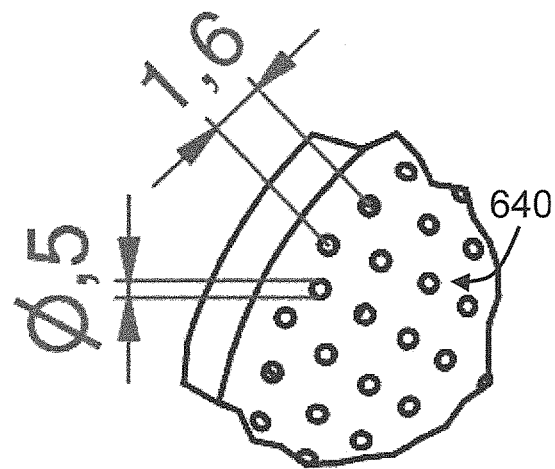
FIG. 11 shows according to an exemplary embodiment of the invention a detailed aspect of a meshed surface area with holes from FIG. 7. The dimensions are in mm.

FIGS. 6-8 especially looking from the top down. The space is defined to fit at least the respective tissue growth materials. In other words, the tissue growth materials are placed over and against their canopy growth surfaces 620 at the medial aspects of canopy growth surfaces 620. In this embodiment, the respective tissue growth material is extended forming a wedge-shape growth material and a canopy (e.g. concave) draped over the canopy growth surfaces 620.

FIGS. 7-11 show an exemplary embodiment of some dimensions of shaper 600, which are not limited to the invention as a person skilled in the art would readily appreciate that heart valves/leaflets would vary in dimensions and shape. The same paper mentioned supra provides guidelines for some of the dimensions.

Depending on the type of cells used with the tissue growth material for shaper 600, there might be a desire to further control the shape and/or spacing between the tissue growth materials draped against the canopy growth surfaces 620. For this purpose, spacer 1700 is designed with three surfaces 1710 distributed/oriented with respect to each other in the same triangular pattern as how canopy growth surfaces 620 are distributed. Side 1720 of spacer 1700 can be placed towards the top of support base 610 and will then sit at the top of the support base 610 (see also FIG. 22). Surfaces 1710 fit in the space left to fit at least the tissue growth material to separate the tissue growth materials supported by each of the canopy growth surfaces 620. In other words, surfaces 1710 will separate the tissue growth materials.

Figure 12:
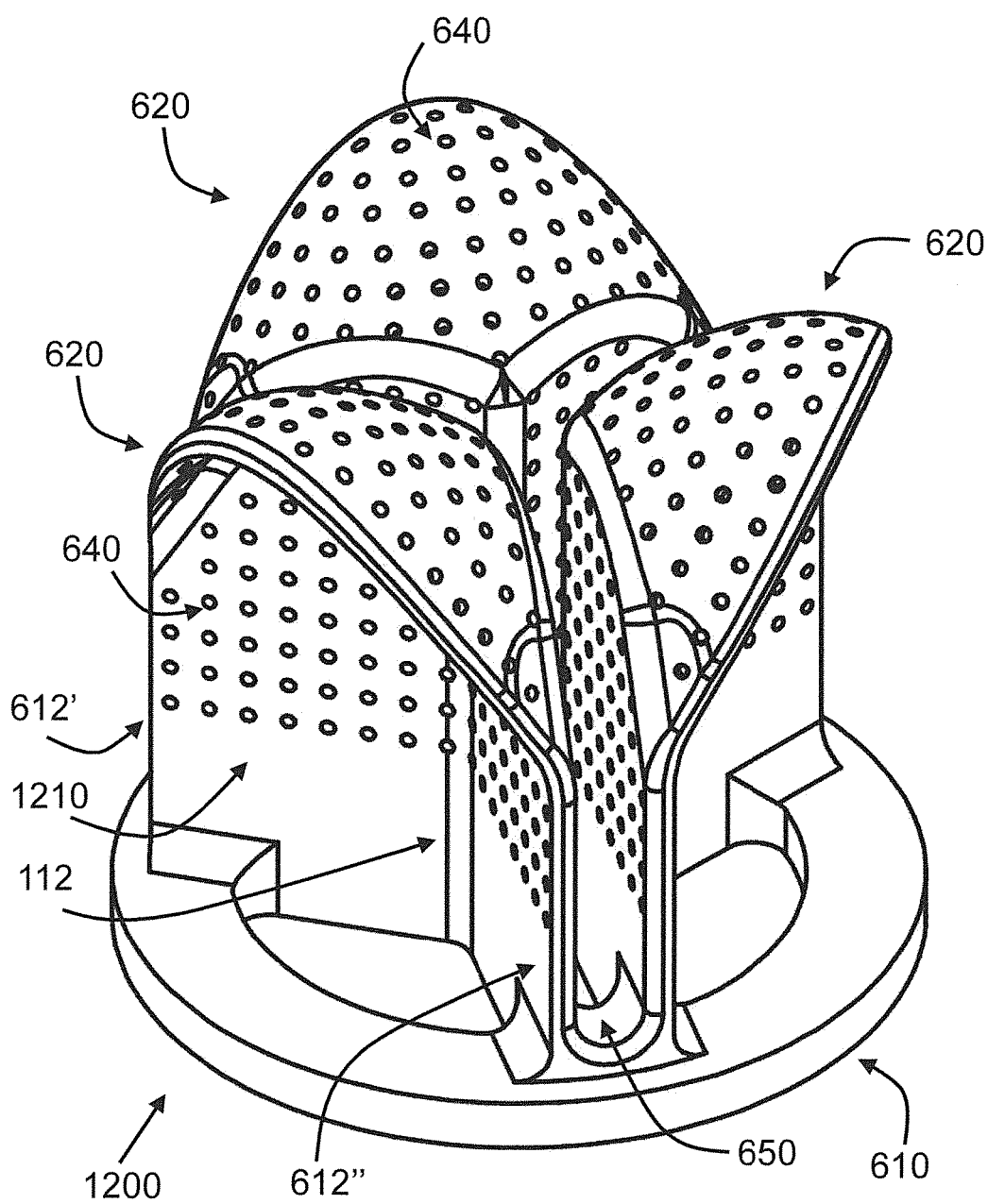
FIG. 12 shows according to an exemplary embodiment of the invention a three dimensional view of a shaper 1200 for maintaining and controlling the shape of tissue growth material for three leaflets of a heart valve during tissue culture.
Figure 13:
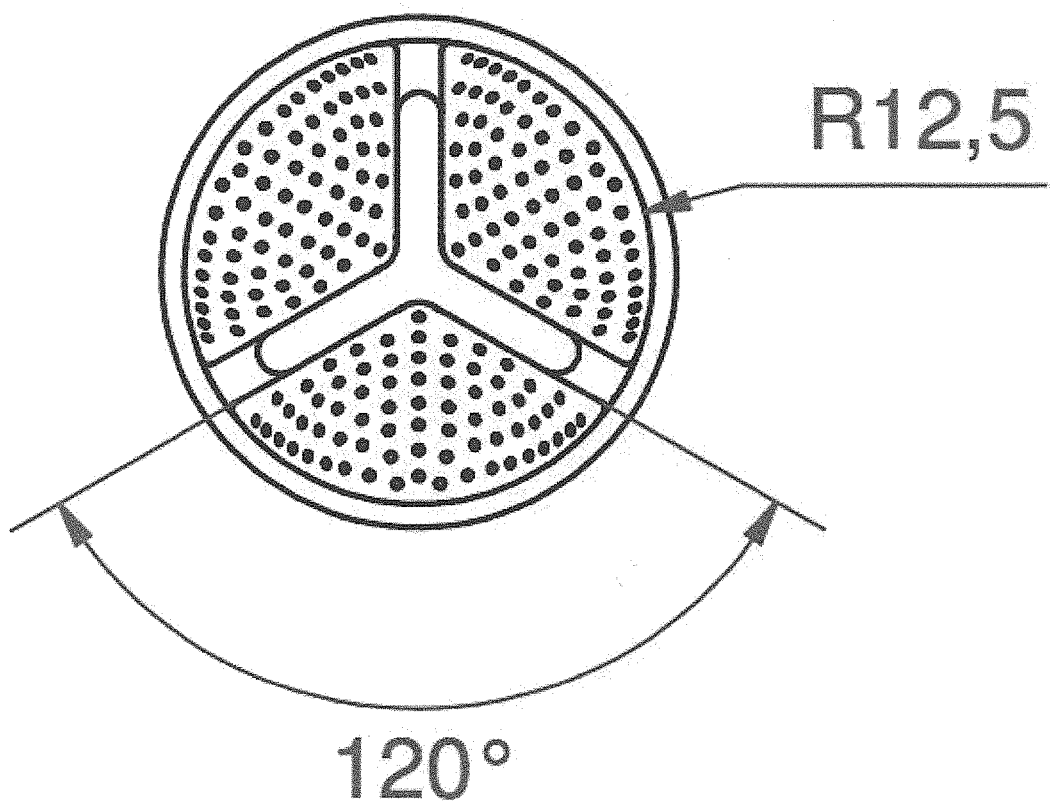
FIG. 13 shows according to an exemplary embodiment of the invention a top view of the shaper as shown in FIG. 12. The dimensions are in mm.
Figure 14:
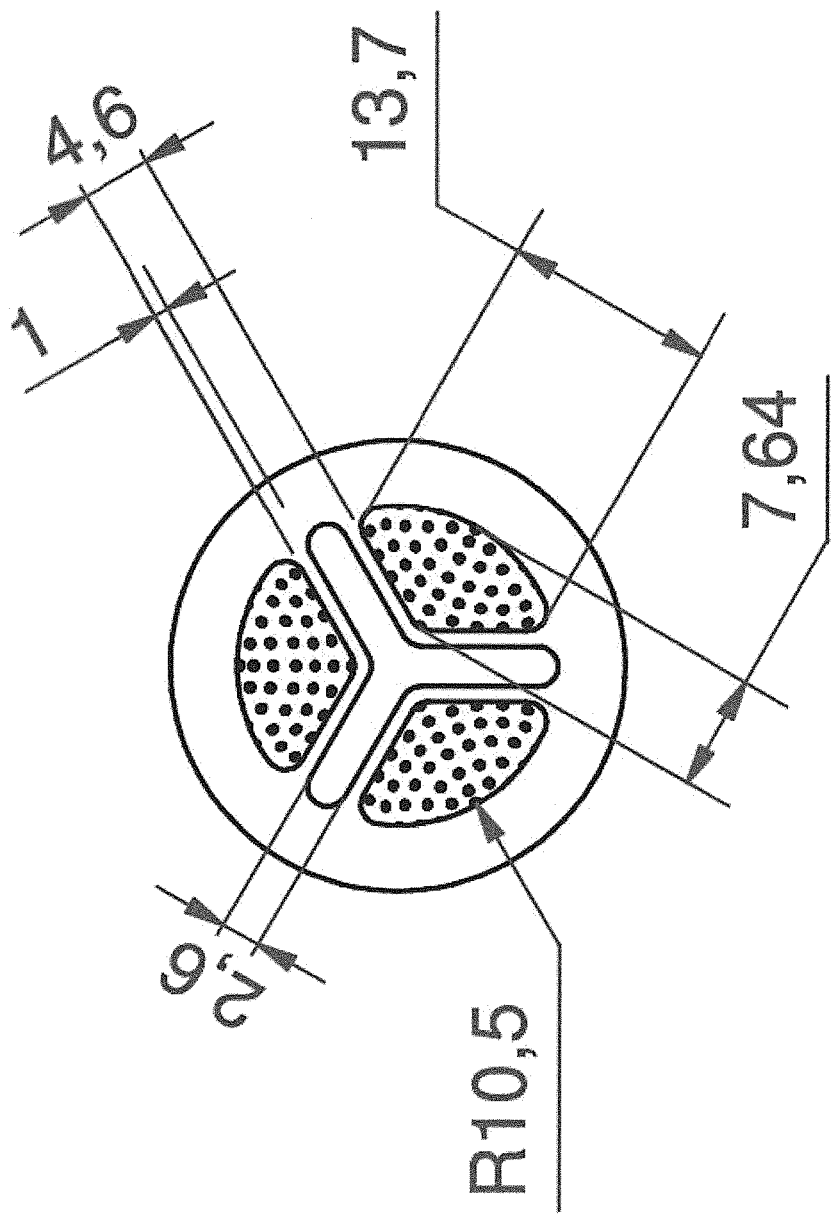
FIG. 14 shows according to an exemplary embodiment of the invention a bottom view of the shaper as shown in FIG. 12. The dimensions are in mm.
Figure 15:
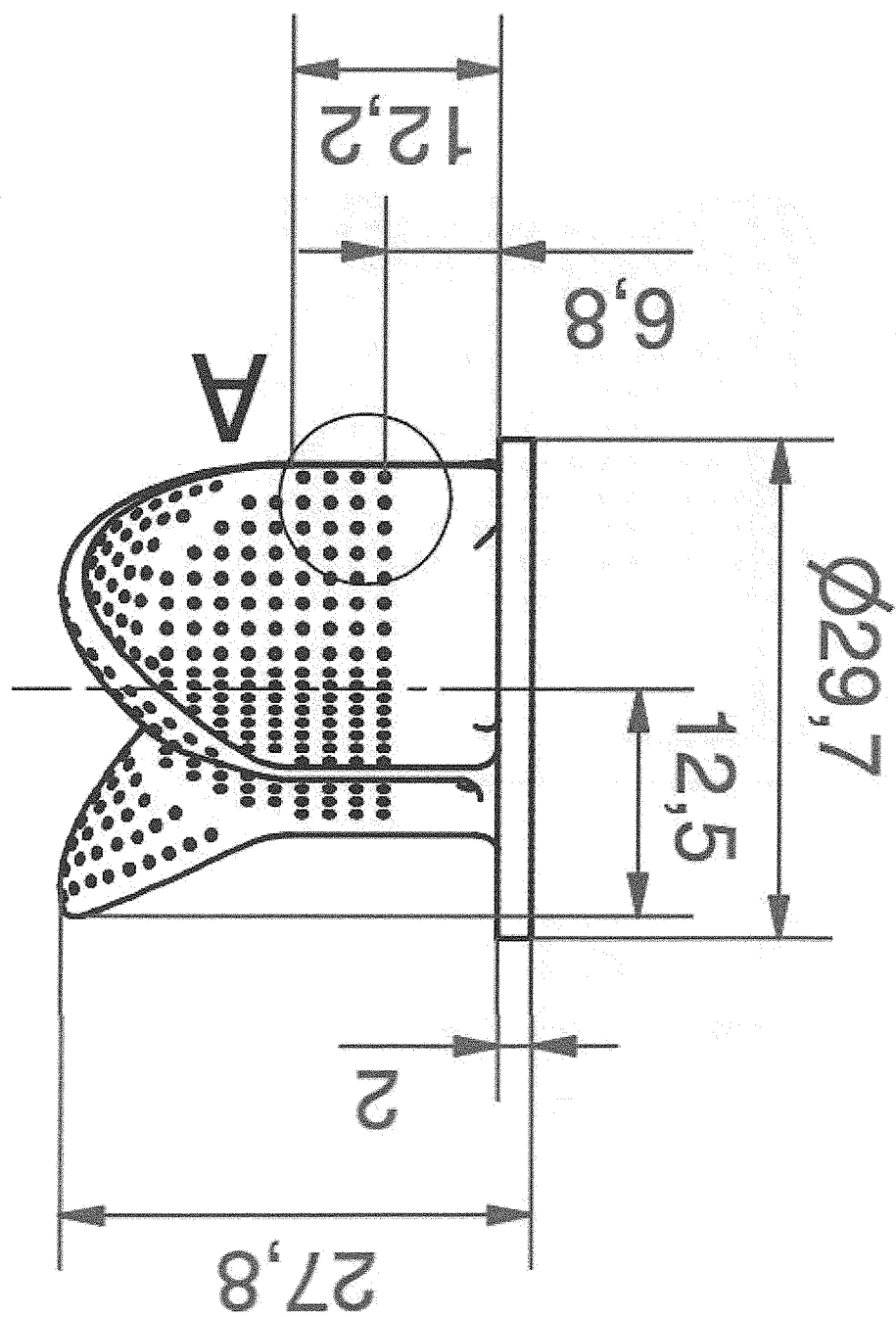
FIGS. 15-16 show according to an exemplary embodiment of the invention side views of the shaper as shown in FIG. 12. The dimensions are in mm.
Figure 16:
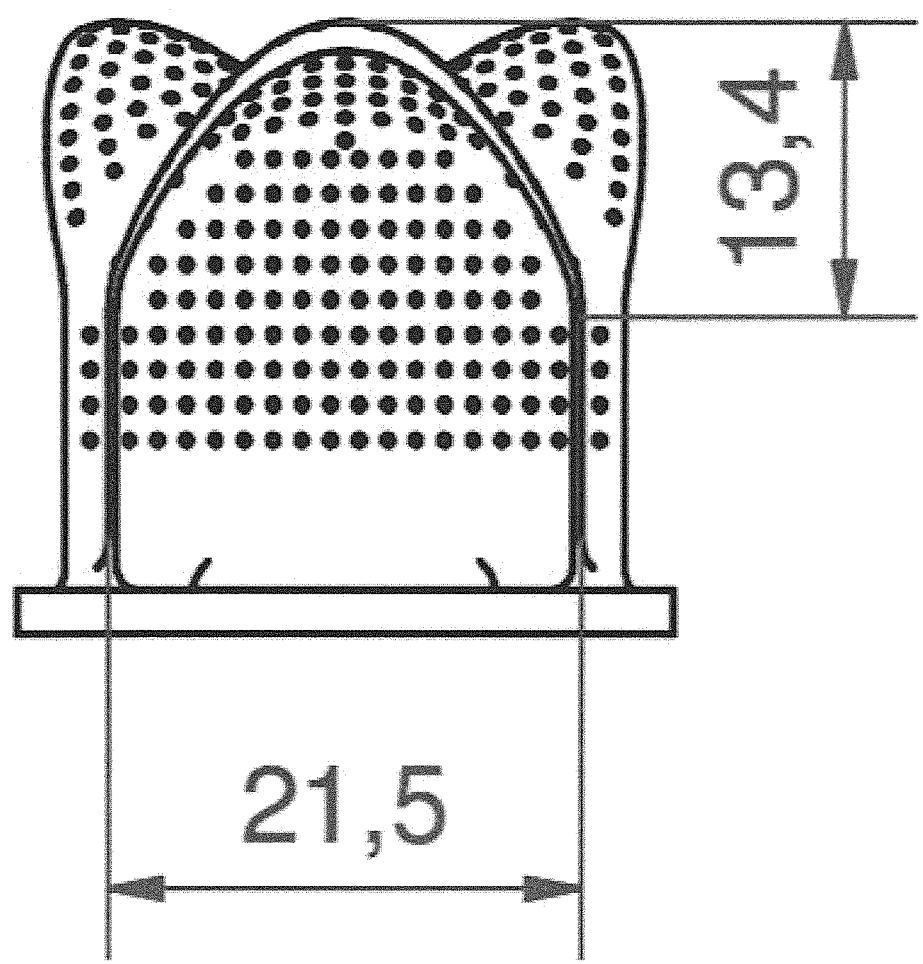
Figure 17:
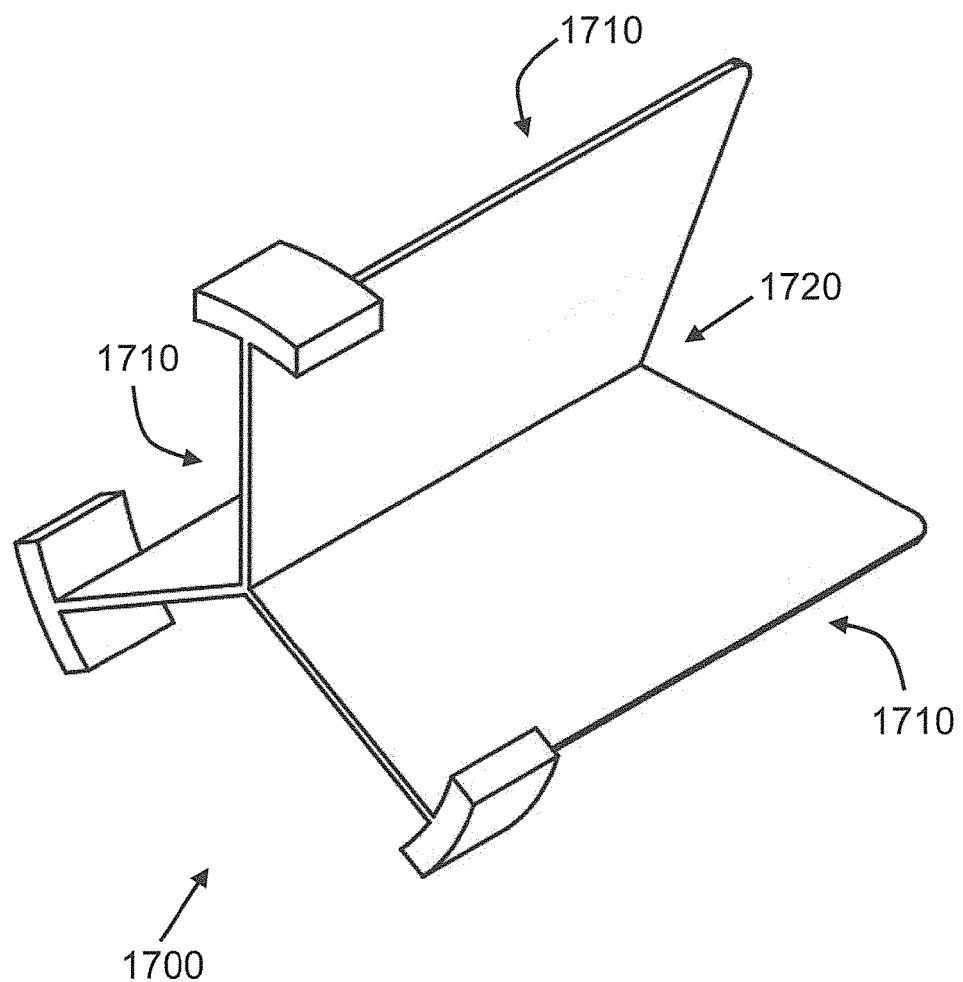
FIG. 17 shows according to an exemplary embodiment of the invention a three dimensional view of a spacer 1700 for further maintaining and controlling the shape of tissue growth material for three leaflets of a heart valve during tissue culture.
Figure 18:
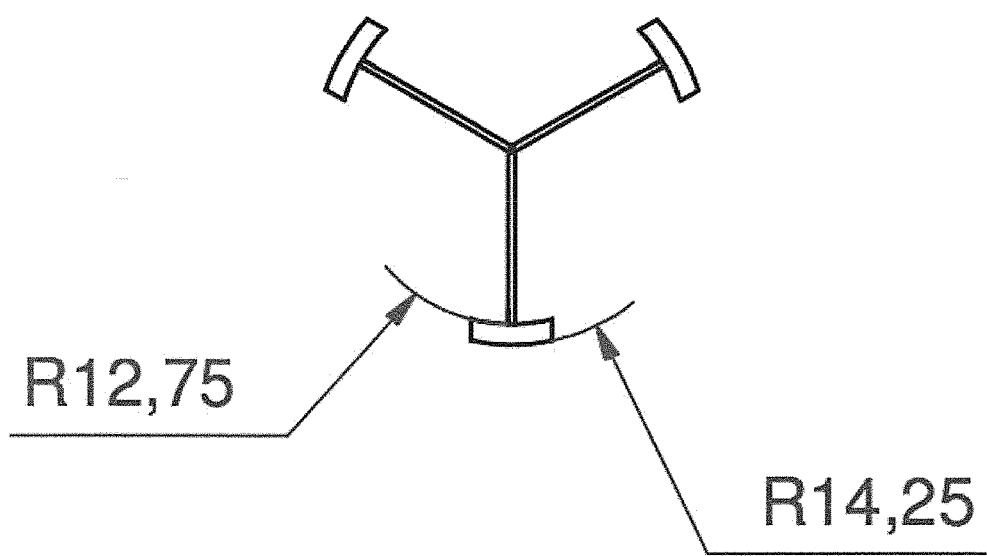
FIGS. 18-19 show according to an exemplary embodiment of the invention top views of the spacer as shown in FIG. 17. The dimensions are in mm.
Figure 19:
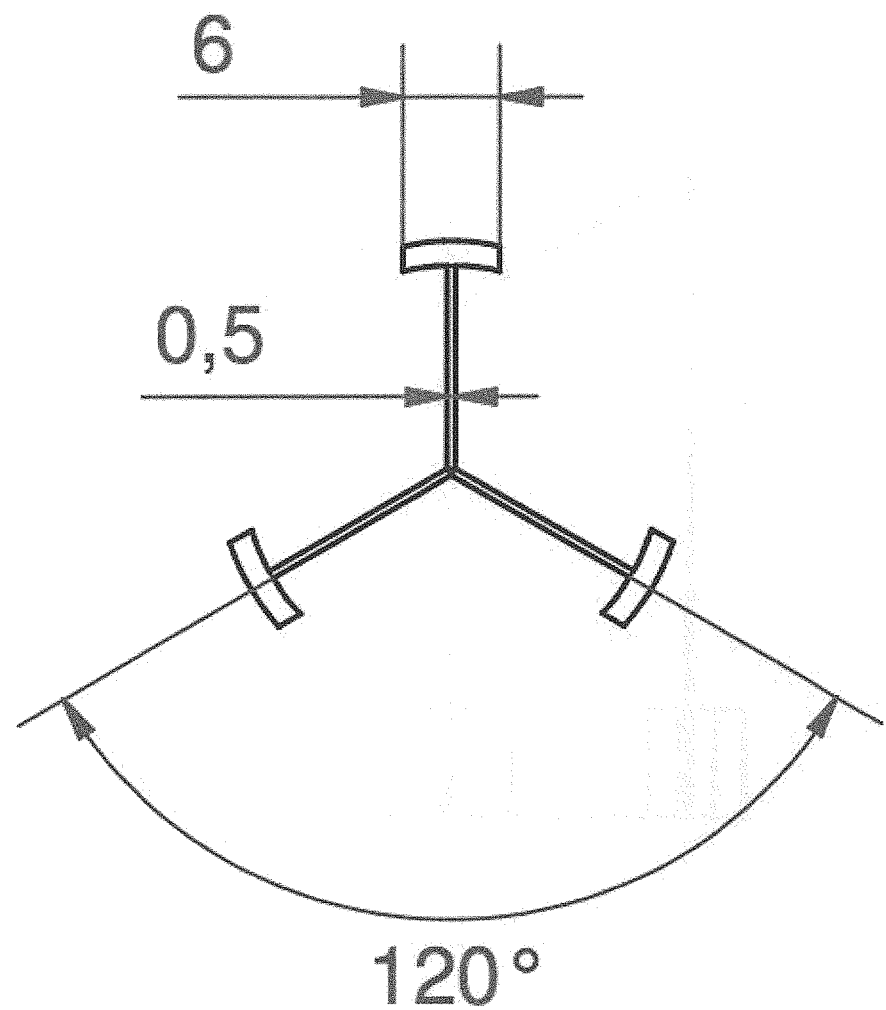
Figure 20:
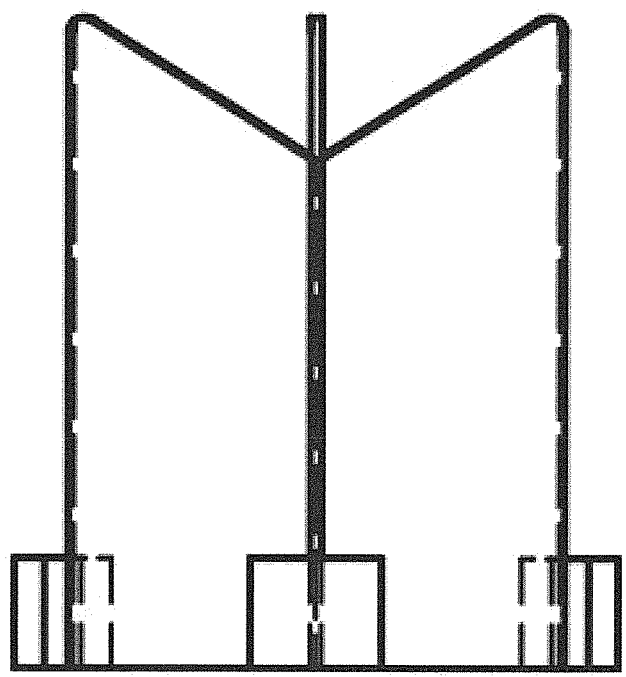
FIGS. 20-21 show according to an exemplary embodiment of the invention side views of the spacer as shown in FIG. 17. The dimensions are in mm.
Figure 21:
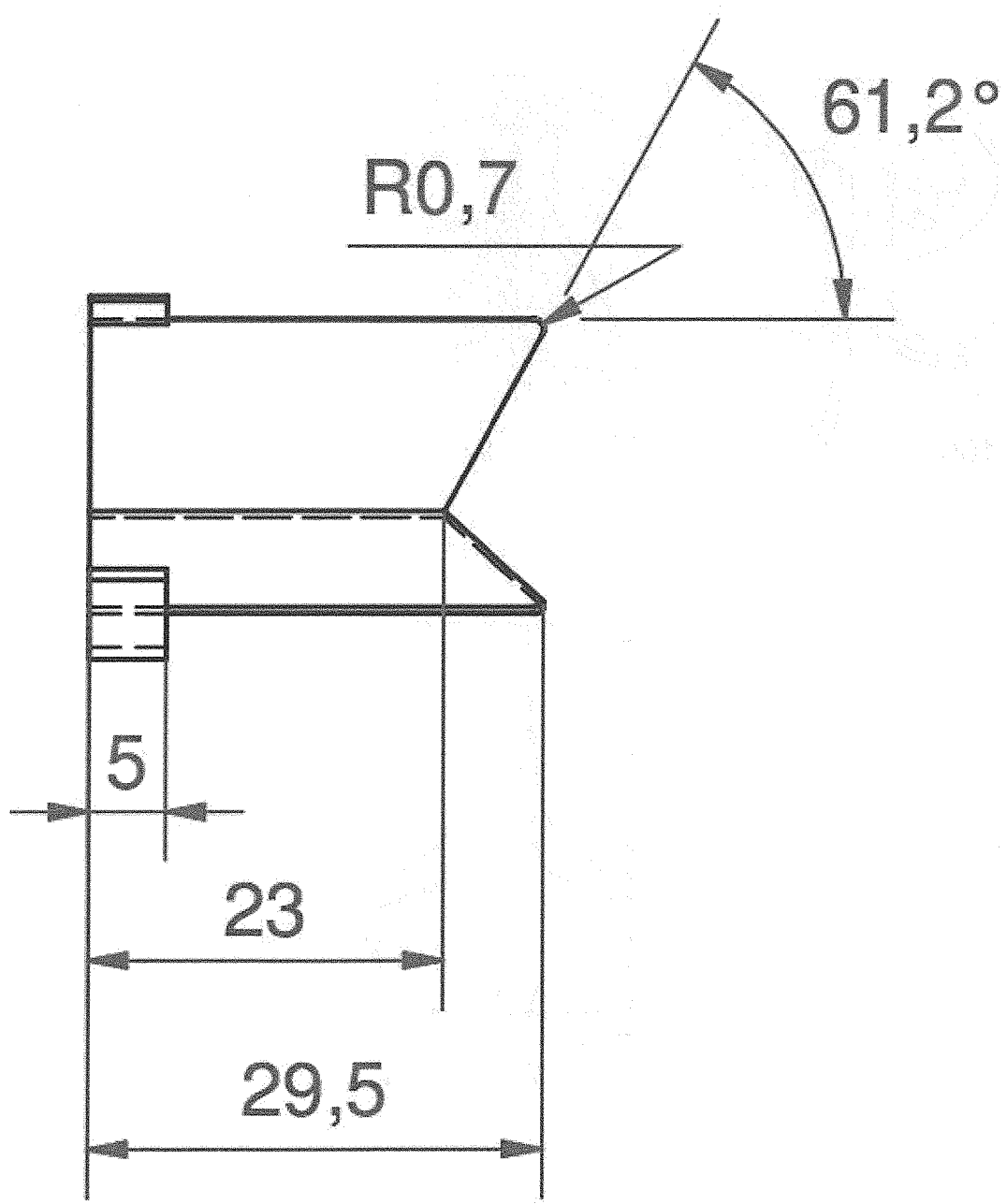

FIGS. 12-16 show a third embodiment of a shaper 1200 for maintaining and controlling heart valve geometry during culture, where shaper 1200 could be viewed as an extension of shapers 100 and 600 by having some structural components in common. Shaper 1200 is intended for a heart valve with three leaflets and distinguishes a support base 610 and three canopy growth surfaces 620 expanded from their respective inner arms 112. It is noted that only one inner arm 112 is indicated in FIG. 12 for clarity purposes.

Shapers 600 and 1200 are similar with the difference that for shaper 1200 each of the canopy growth surfaces 620 further span to the base of support surface 610 with meshes surfaces 1210 between the respective outer arms 612', 612" and inner arm 112. Only one of the meshed surfaces is indicated for clarity purposes. It is also noted that a wedge shaped surface forms the basis for each of the concave parts of the canopy growth surfaces.

Another difference is that the meshes surface 1210 have holes, like holes 640, to allow exchange of nutrients. Each of these canopy growth surfaces 620 is capable of supporting the respective growth material. Similar to shaper 600, spacer 1700 can be used for shaper 1200 to fit in the space 650 left to fit at least the tissue growth material to separate the tissue growth materials supported by the meshed surfaces.

FIGS. 13-16 show an exemplary embodiment of some dimensions of shaper 1200, which are not limited to the invention as a person skilled in the art would readily appreciate that heart valves/leaflets would vary in dimensions and shape. The same paper mentioned supra provides guidelines for some of the dimensions.

Figure 22:
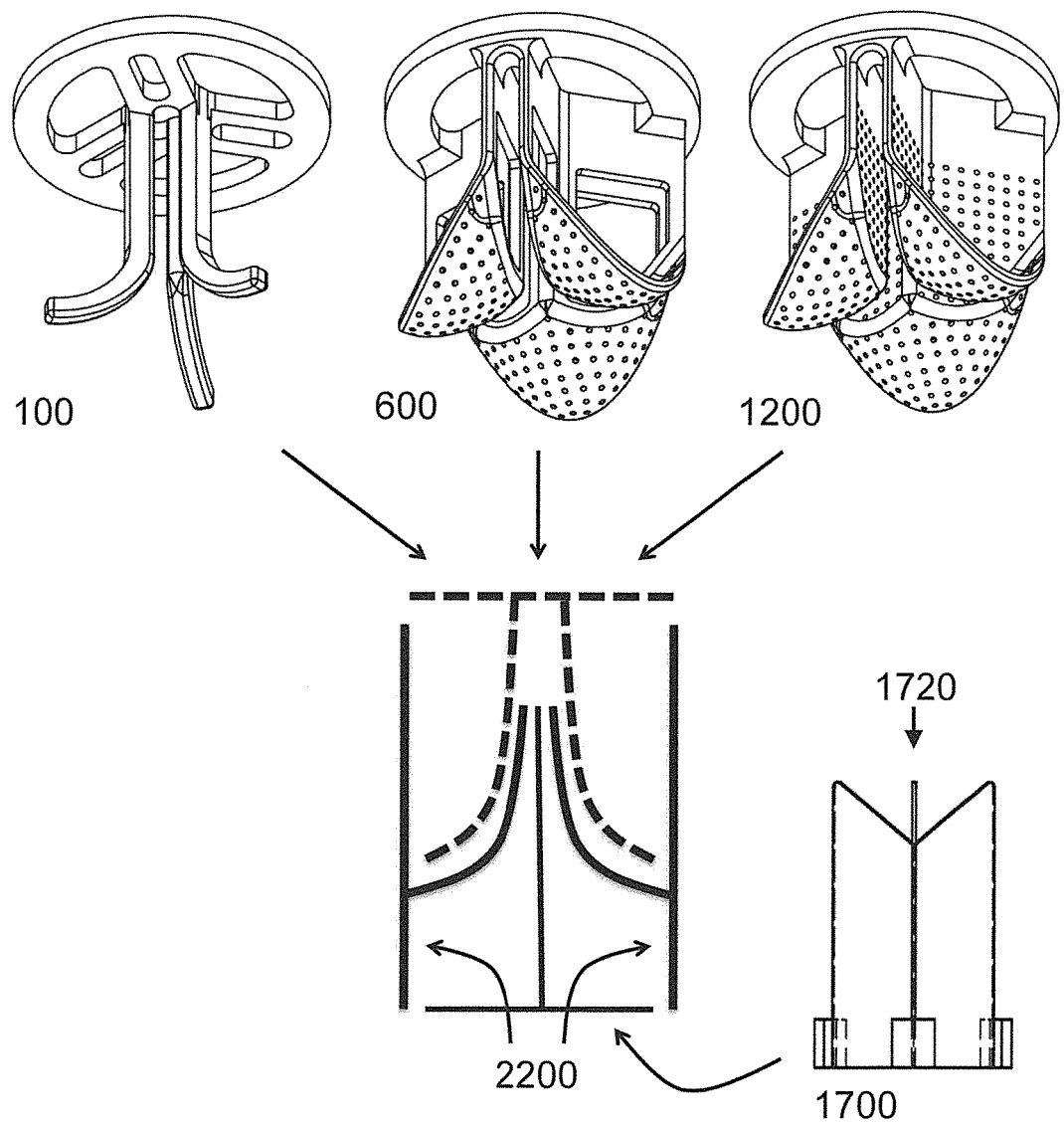
FIG. 22 shows according to an exemplary embodiment of the invention the various shapers 100, 600 and 1200 with spacer 1700, and tissue growth material 2200 and how they fit and can be used together.

In summary, FIG. 22 shows the various shapers 100, 600 and 1200 with spacer 1700, and tissue growth material 2200 and how they fit and can be used together. There are various variations one could imagine, such as that these embodiments can be constructed for a single-leaflet heart valve, bi-leaflet (two leaflet) heart valve or multiple-leaflet heart valve. The design principles for these different heart valves would be similar to the tri-leaflet heart valve with the difference of the number of inner arms for shaper 100, the number of canopy growth surfaces for shaper 600 and 1200, the shape of the space with the growth surfaces and various others as a person skilled in the art would readily appreciate. In addition, dimensions (including the radius/angles of the canopy growth surfaces) shown in the exemplary embodiments could be varied to fit the desired objective for the tissue engineered heart valves.

The manufacturing of the inserts could be via conventional computer numerical control (CNC) milling technology with biocompatible materials such as polyether ether ketone (PEEK) or via rapid prototyping techniques like three-dimensional printing with materials such as acrylonitrile butadiene styrene (ABS) or more biocompatible materials such as PLA. However, other conventional manufacturing techniques would still suffice. In addition, the shapers and spacers could be made as modular components that could be assembled to for example come up for a single-leaflet, bi-leaflet or tri-leaflet design.

Circumferential Collagen Alignment

Figure 23:
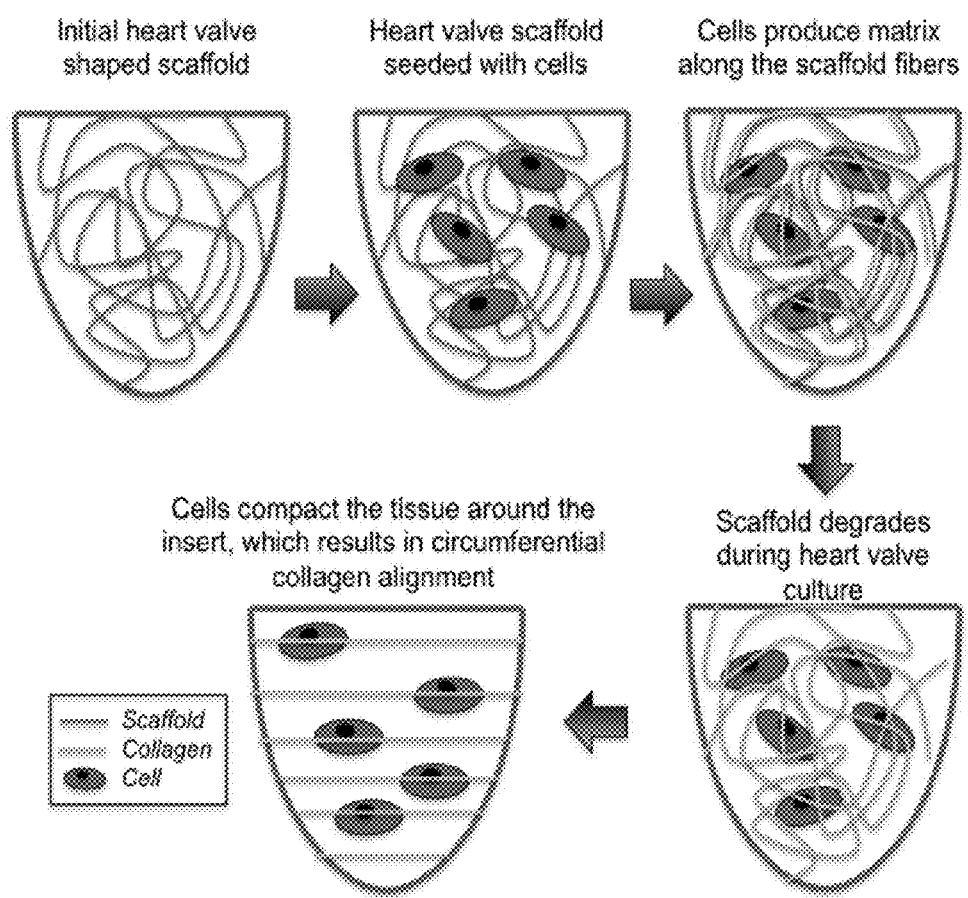
FIG. 23 shows according to an exemplary embodiment of the invention a change from random collagen orientation towards circumferential aligned collagen orientation, due to the leaflet shaper insert during culture.

Circumferential collagen alignment in TEHVs will result in radial leaflet stretch while being hemodynamically loaded, which is beneficial for the opening and closing behavior of the valve. As shown in FIG. 23, the starter matrix of the TEHV contains mainly randomly organized scaffold fibers. When the cells are seeded onto the construct, they will start producing randomly organized collagen matrix along these scaffold fibers. During culture, the scaffold material will hydrolyze and lose mechanical functionality. From this point on cells will start pulling in the direction of constrained. Since the leaflet shaper insert is a rigid body, cells will compact around this insert and realign the collagen in the direction of constrain. This will result in circumferentially aligned collagen orientation (FIG. 23).

Static Valve Culture

Currently TEHVs are being cultured in a sophisticated bioreactor system. This system is regulating pulsatile pressures onto the leaflets in combination with regulated medium flow to enhance tissue formation. We found out that by using the insert as presented herein during culture, the bioreactor system can be replaced by a simple jar. Since the insert is required to maintain the initial heart valve geometry, it is hampering the pulsatile pressures exerted on the leaflets, which makes the main function of the bioreactor system redundant or obsolete. It seems that when the fluid flow is maintained, it would still be possible to culture functional TEHVs. This finding can have a big impact in the way TEHVs can be produced in a future commercial way. Without the use of a complicated bioreactor system, valve production can be up scaled easily and will lower the production costs.

Results

Figure 24:
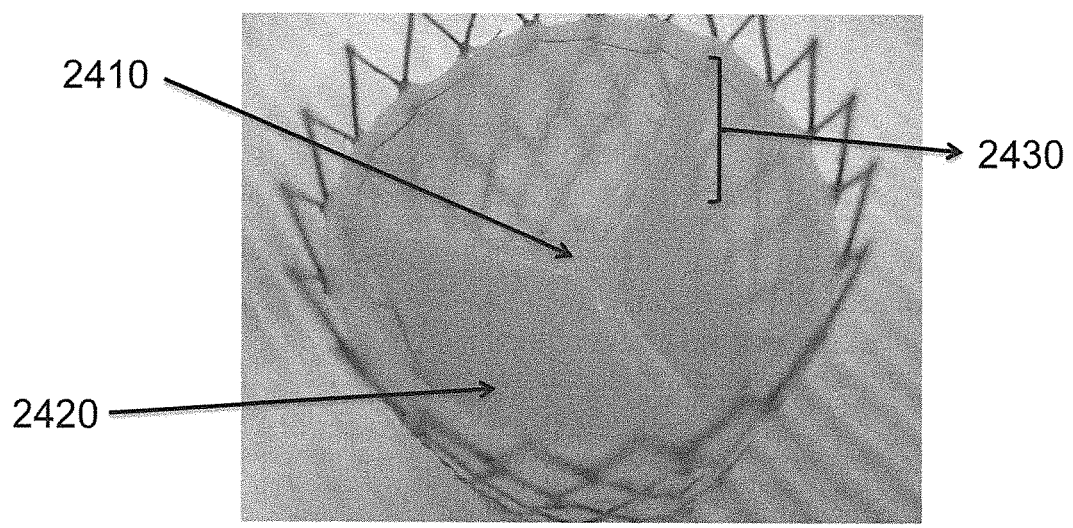
FIGS. 24-25 show according to exemplary embodiments of the invention in vitro results of TEHVs cultured with the use of, for example, but not limited to shaper 1200.
Figure 25:
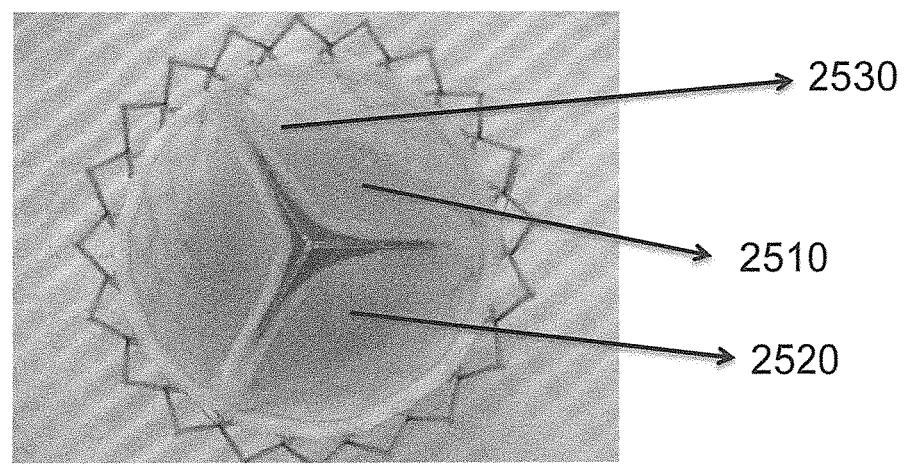

FIGS. 24-25 show examples of in vitro results of TEHVs cultured with the use of for example shaper 1200. After removal of shaper 1200 the TEHV maintained the imposed geometry. FIG. 24 shows results for a closed configuration with no leaflet retraction 2410, maintenance of leaflet curvature 2420 and a controlled coaptation area 2430. FIG. 25 shows results for an open configuration with leaflets shaped around the shaper insert 2510, maintenance of leaflet curvature 2520 and a controlled coaptation area 2530.

Figure 26:
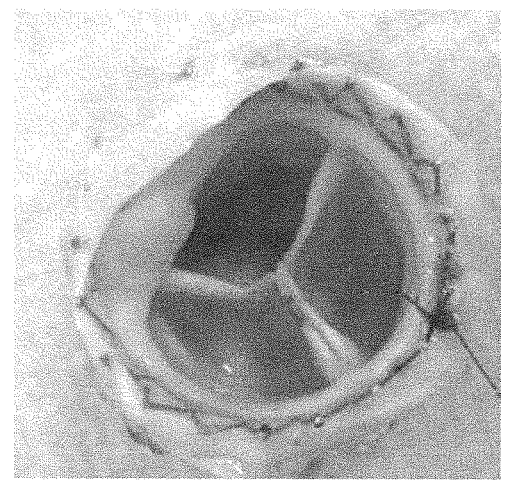
FIG. 26 shows according to an exemplary embodiment of the invention long term in vivo results of TEHVs cultured with the use of, for example, but not limited to shaper 1200.

FIG. 26 shows an example of long term in vivo results of TEHVs cultured with the use of for example shaper 1200. Up to 24 weeks, the heart valve maintained its initial geometry and showed no signs of leaflet retraction. These results confirm that the initial geometry of the heart valve after culture is decisive for the final long-term outcome, which can only be obtained by using the leaflet shaper insert during culture.

What is claimed is:

1. A heart valve culturing device, wherein the heart valve comprises at least two leaflets, the device comprising:
   a. a support base; and
   b. at least two inner arms each capable of supporting a tissue growth material to from one of the leaflets,
      wherein each of the inner arms has a first portion and a second portion,
      wherein the first portion is disposed normal to the support base and disposed proximal to a center of the support base,
      wherein the second portion is nonlinear and disposed distal to the support base and blends away from the center of the support base,
      wherein the at least two inner arms are spaced from each other defining enough space to fit at least the respective tissue growth materials;
      the device further comprising a spacer to fit in said space and to separate the tissue growth materials supported by each of the linear portions of the inner arms;
      the spacer comprises at least two planar surfaces, all of the planar surfaces having a common intersection line, the intersection line being substantially parallel to and circumferentially surrounded by said linear portions of the inner arms.

2. The heart valve cell culturing device of claim 1, wherein each of the inner arms further comprises a canopy growth surface expanded from the second portion of the respective inner arms,
   wherein each of the canopy growth surfaces define a concave surface when moving away from the center of the support base in outer direction,
   wherein each of the canopy growth surfaces is supported by the first portions of the inner arms and a pair of outer arms defined for each of the inner arms,
   wherein each of the outer arms have a first portion disposed normal to the support base and disposed distal to the center of the support base, and
   wherein each of the canopy growth surfaces are capable of supporting the respective growth materials.

3. The heart valve cell culturing device of claim 2, wherein the canopy growth surfaces comprise holes to allow exchange of nutrients.

4. The heart valve cell culturing device of claim 2, wherein each of the canopy growth surfaces further span to the base of the support surface along the radial separation of the respective outer arms and inner arm, wherein each span capable of supporting the respective growth material.

5. The heart valve of cell culturing device of claim 2, wherein each of the canopy growth surfaces further span to the base of the support surface and form meshed surfaces between the respective outer arms and inner arm each capable of supporting the respective growth material.

6. The heart valve cell culturing device of claim 5, wherein the meshed surfaces comprise holes to allow exchange of nutrients.

7. The heart valve cell culturing device of claim 2, wherein the combinations of each of the first portions of the inner arms with their respective pair of outer arms define wedge-shape growth surfaces each capable of supporting the respective growth material.

8. The heart valve cell culturing device of claim 7, wherein the wedge-shape growth surfaces comprise holes to allow exchange of nutrients.

9. The heart valve cell culturing device of claim 1, wherein the at least two inner arms have three inner arms and the pattern is a triangular pattern.

* * * * *